United States Patent [19]

Van Iten et al.

[11] Patent Number: 5,507,735
[45] Date of Patent: Apr. 16, 1996

[54] ABSORBENT ARTICLE HAVING MOVEABLE ATTACHMENT MEANS

[75] Inventors: Thomas P. Van Iten; Frederich O. Lassen, both of Neenah, Wis.

[73] Assignee: Kimberly-Clark Corporation, Neenah, Wis.

[21] Appl. No.: 286,717

[22] Filed: Aug. 5, 1994

[51] Int. Cl.$^6$ .................................................. A61F 13/15
[52] U.S. Cl. ...................... 604/385.1; 604/386; 604/387; 604/393; 604/400
[58] Field of Search .............................. 604/385.1, 386, 604/387, 392, 393, 400

[56] References Cited

U.S. PATENT DOCUMENTS

| | | |
|---|---|---|
| 3,367,334 | 2/1968 | Testa . |
| 3,420,234 | 1/1969 | Phelps . |
| 3,532,097 | 10/1970 | Jones . |
| 3,570,492 | 3/1971 | Bettencourt . |
| 3,593,717 | 7/1971 | Jones . |
| 3,654,929 | 4/1972 | Nilsson et al. . |
| 3,783,869 | 1/1974 | Schnipper . |
| 3,911,921 | 10/1975 | Svensson . |
| 3,954,107 | 5/1976 | Chesky et al. . |
| 4,372,312 | 2/1983 | Fendler et al. . |
| 4,405,310 | 9/1983 | Karami ..................................... 604/383 |
| 4,425,130 | 1/1984 | DesMarais .............................. 605/389 |
| 4,433,972 | 2/1984 | Malfitano . |
| 4,531,945 | 7/1985 | Allison .................................... 604/378 |
| 4,536,181 | 8/1985 | Cook ....................................... 604/387 |
| 4,576,597 | 3/1986 | Hlaban ................................... 604/390 |
| 4,605,405 | 8/1986 | Lassen .................................... 604/389 |
| 4,623,341 | 11/1986 | Roeder ................................. 604/385.1 |
| 4,631,062 | 12/1986 | Lassen et al. . |
| 4,846,824 | 7/1989 | Lassen et al. ......................... 604/385.1 |
| 4,950,263 | 8/1990 | Lewis .................................... 604/385.1 |
| 5,057,096 | 10/1991 | Faglione ............................... 604/385.1 |
| 5,169,394 | 12/1992 | Jean ...................................... 604/385.1 |
| 5,236,428 | 8/1993 | Zajaczkowski .................. 604/385.1 X |

FOREIGN PATENT DOCUMENTS

| | | |
|---|---|---|
| 0343941A2 | 11/1989 | European Pat. Off. . |
| 5-49660 | 3/1993 | Japan ..................................... 604/387 |

Primary Examiner—Mary Beth Jones
Attorney, Agent, or Firm—Mark L. Davis

[57] ABSTRACT

A sanitary napkin assembly is disclosed having a second absorbent pad that is superposed over and movably secured to a first absorbent pad. Each absorbent pad has a centrally positioned, longitudinal axis. The securement device securing the second absorbent pad to the first absorbent pad allows the second absorbent pad to move along one of the longitudinal axes and preferably permits the second absorbent pad to rotate through an angle of about 90 degrees.

11 Claims, 4 Drawing Sheets

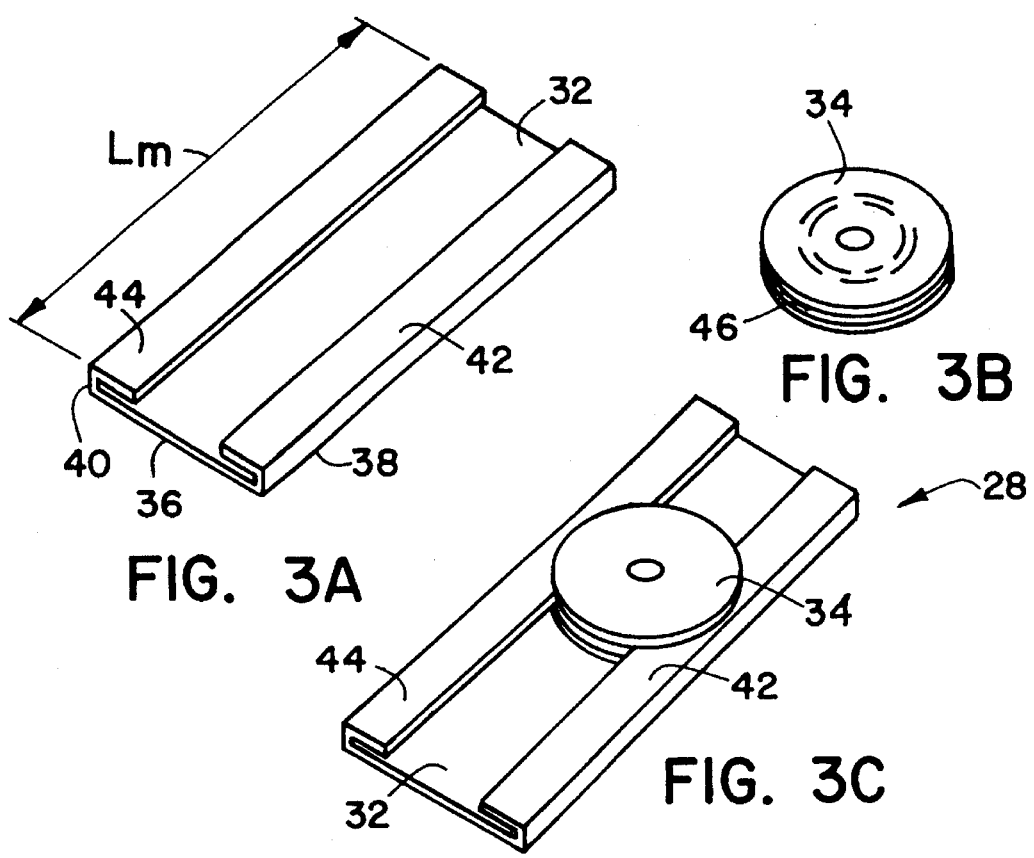
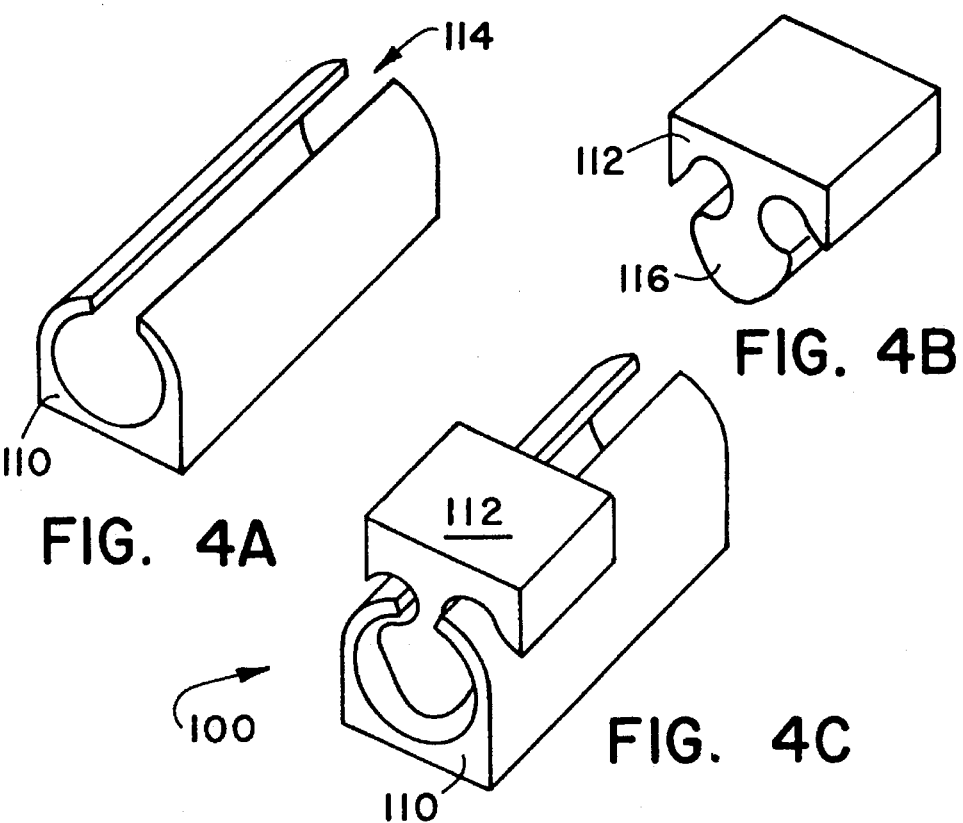

ABSORBENT ARTICLE HAVING MOVEABLE ATTACHMENT MEANS

FIELD OF THE INVENTION

This invention relates to an absorbent article having dual absorbent pads and more particularly to a sanitary napkin having dual absorbent pads that are movably attached to each other.

BACKGROUND OF THE INVENTION

A wide variety of absorbent structures, devices or appliances configured for the absorption of body fluids such as menses, blood, urine, and the like are well known. Disposable products of this type generally comprise some sort of good permeable topsheet or cover material, an absorbent core, and a fluid-impermeable baffle material.

Traditionally, all sanitary napkins have suffered from "distortion failures." These failures generally result because sanitary napkins are not three-dimensionally shaped and are not made to continuously dynamically conform to the perineal and vulva areas of the wearer, particularly when the wearer is in motion. Generally, the torque forces exerted on the side of the napkin distort the discharge target area on the face of the napkin and may provide a substantial number of napkin failures due to the angle at which the menses strikes the distorted surface.

Furthermore, positioning a sanitary napkin relative to the body of the wearer is an important consideration. In the early years, napkins were affixed about the body wearer by means of a belt or tab. Over the last decade or so, sanitary napkins have now routinely been secured within or to the undergarment of the user. One drawback of the current napkins is that movement, particularly vigorous movement such as, rapid walking or running, yields motion between the body of the wearer relative to the undergarment. Securing a sanitary napkin to the wearer's undergarment, therefore, translates under ordinary circumstances into relative motion between the wearer's body and the napkin itself. This movement typically causes the sanitary napkin to acquire an undesirable shape, such as bunching, twisting, roping, etc. which adversely affects the sanitary napkin's performance. More specifically, movement and particularly vigorous movement yields motion between the wearer's body, and particularly within the vulvar region, relative to the undergarment. In turn this can lead to heightened discomfort due to chafing, rubbing and perhaps even more intense irritation about highly sensitive tissues of the wearer. Now a sanitary napkin assembly has been invented which overcomes these disadvantages.

SUMMARY OF THE INVENTION

Briefly, the present invention relates to an absorbent article assembly having a first absorbent pad and a second absorbent pad in a superposed position over the first absorbent pad. Affixed to at least one of the absorbent pads is a securement device for movably securing the absorbent pads together. The moveable securement device is positioned intermediate the first absorbent pad and the second absorbent pad. In one embodiment, the securement device includes a second member engaged with a first member. The first member is located along a centrally positioned, longitudinal axis of the first absorbent pad and the second member is located along a centrally positioned, longitudinal axis of the second absorbent pad. The moveable securement device allows the second absorbent pad to be dynamically repositioned along at least one of the longitudinal axis of the absorbent pads. In a preferred embodiment, the securement device is at least partially rotatable, thereby allowing the second absorbent pad to slidably and rotatably move along one of the longitudinal axes. In one aspect of the invention, the securement device is designed so that the first and second members can be readily disengaged so that either pad may be used by the wearer alone.

A general object of this invention to provide an absorbent article having dual absorbent pads. A more specific object of this invention is to provide an absorbent article having a securement device which allows the second absorbent pad to be independently repositioned relative to the first absorbent pad.

Another object of the invention is to provide for a sanitary napkin assembly having a plurality of separate absorbing portions.

Another object of the invention is to provide for a sanitary napkin assembly wherein the second absorbent pad is of a dimension smaller than the first absorbent pad and which is designed to contact the body of the wearer.

Yet another object of the invention is to provide a sanitary napkin having first and second absorbent pad in which one absorbent pad can be readily adjusted by the user with the absorbent pad closest to the wearer responding to dynamic motion of the wearer.

BRIEF DESCRIPTION OF THE DRAWINGS

The invention will now be described in detail in conjunction with the accompanying drawings, in which:

FIG. 3 is a partial cut-away of a perspective view of the absorbent pad assembly illustrating the moveability of the securement device.

FIG. 3A is a plan view of the first member of one embodiment of the securement device.

FIG. 3B is a plan view of the second member of the securement device.

FIG. 3C is a plan view of the securement device showing the first and second members of FIGS. 3A and 3B engaged.

FIG. 4A is a plan view of the first member of an alternate embodiment of the securement device.

FIG. 4B is a plan view of the second member of an alternate embodiment of the securement device.

FIG. 4C is a plan view of the alternate embodiment of the securement device showing the first and second members 4A and 4B engaged.

DETAILED DESCRIPTION OF THE PREFERRED EMBODIMENT

Figure 1:
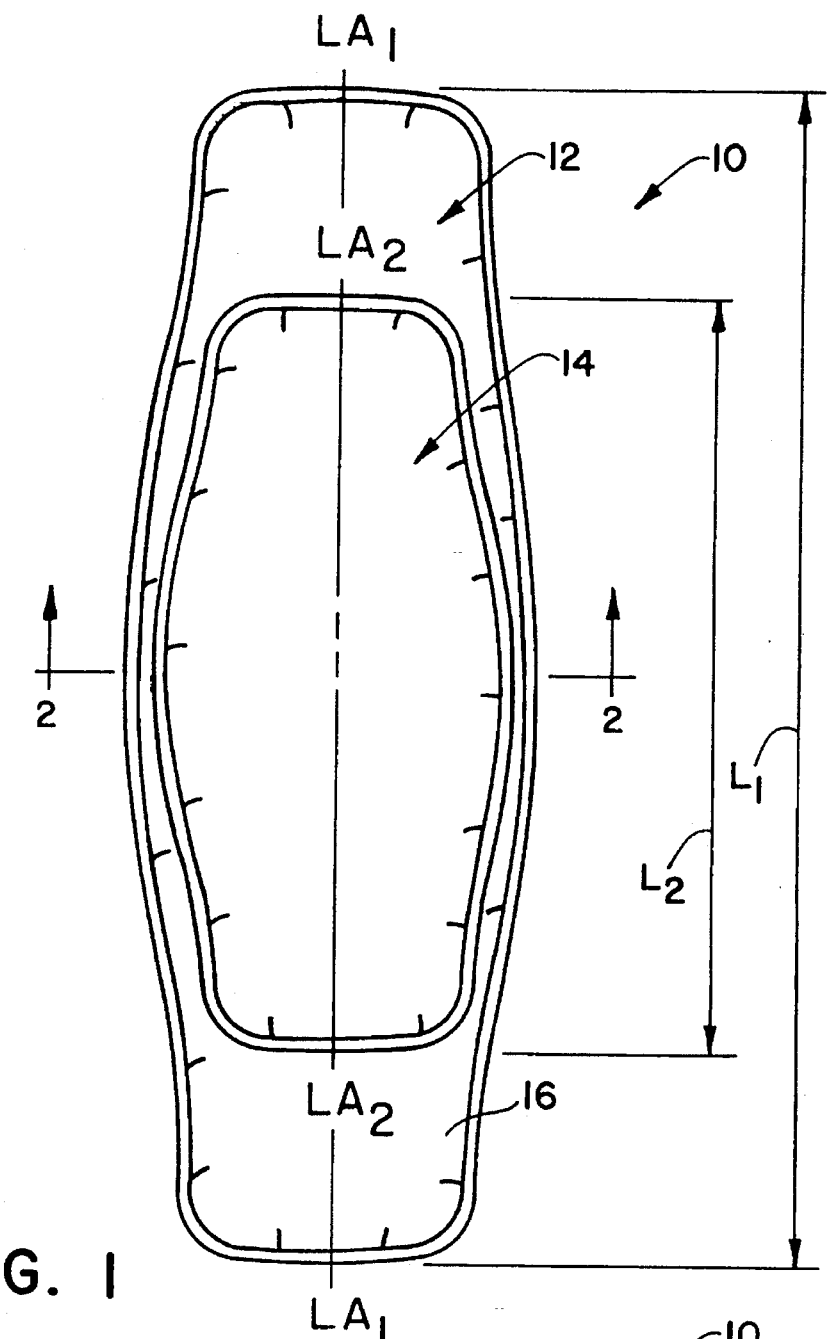
FIG. 1 is a top plan view of the dual absorbent pad assembly showing the superposed positioning of the pads.
Figure 2:
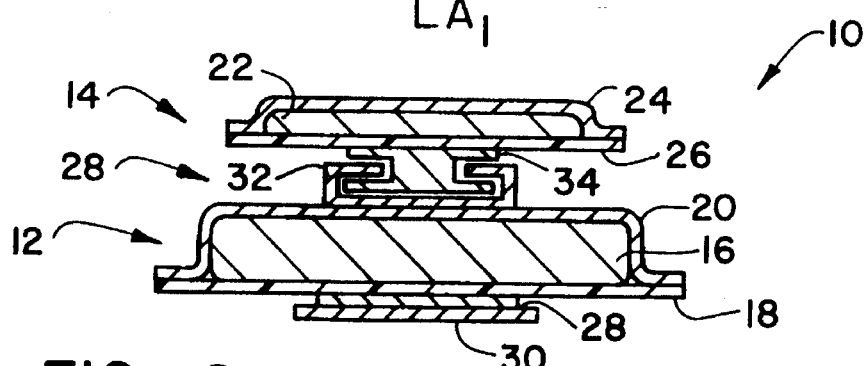
FIG. 2 is a cross-sectional view of FIG. 1 taken along line 2—2 showing a cross-section of the first and second absorbent pads and a cross-section of one embodiment of the securement device.

This invention relates to absorbent articles, such as catamenial devices, incontinence devices, disposable diapers, and the like, and will be described as a sanitary napkin. Regarding the accompanying drawings, like reference numerals will designate similar parts throughout the various views. Turning to FIGS. 1 and 2, a sanitary napkin assembly designed generally as 10, is shown which includes a first absorbent pad 12 and a second absorbent pad 14. The first absorbent pad 12 includes an absorbent 16, a baffle 18 and optionally, a cover 20. As is well known, the absorbent 16, the baffle 18 and cover 20 each have a body-facing side and a garment-facing side. The body-facing side is that surface which faces the wearer's body during use, while the garment-facing side is that surface which faces away from the wearer's body and towards the undergarment. Thus, in a typical disposable absorbent article, the body-facing surface of the absorbent 16 resides adjacent to the garment-facing surface of the cover 20.

The second absorbent pad 14 includes a second absorbent 22, a second cover 24 and optionally, a second baffle 26. In the case where the second absorbent pad 14 includes a baffle 26, it can be advantageous to aperture the baffle 26 (not specifically shown in the figures herein). The apertures can be of any geometric design and dimension which allows for absorbed body fluids in the second absorbent pad 14 to flow to the first absorbent pad 12. This advantageously allows for a more complete utilization of the absorbent capacity of the sanitary napkin assembly 10.

Since the materials used in the construction of the first and second absorbent pads 12 and 14 are preferably similar, only the first absorbent pad 12 will be hereinafter described. The cover 20 is designed to contact the wearer's body and therefore should be compliant, soft feeling and non-irritating to the wearer's skin. It can be made from any of the materials conventional for this type of use. Non-limiting examples of such material include a woven or nonwoven, natural or synthetic material which is easily penetrated by body fluids. Other examples include thermoplastic polymer films made from fibers or filaments of polyethylene or polypropylene as well composites of films and nonwoven materials. It can also be beneficial to aperture or emboss the cover 20 (not shown) to increase the rate at which the body fluids can penetrate down through it and into the absorbent 16. In a preferred embodiment of the present invention, the outer or body-facing surface of the cover 20 is treated with a surfactant. This renders the top surface more hydrophilic and allows liquids insulting the cover 20 to penetrate the cover 20 faster than if the surface were not treated. This diminishes the likelihood that menstrual fluid will flow off the cover 20 rather than being absorbed by the absorbent 16. For example, suitable medically safe surfactants include: sodium alkyl sulfosuccinates; polyoxyethylene alleanols, phenols and sorbitan esters of $C_{12-13}C_2O$ fatty acids; alkylammonium alkyl sulfates and mixtures thereof. It is preferred that the surfactant be distributed substantially evenly and completely across the top surface of the cover 20. This can be accomplished by any of the commonly known techniques of those of ordinary skill in the art. For example, the surfactant can be applied to the cover 20 by spraying, padding, or using transfer rolls.

The absorbent 16 may be comprised of any of the well known absorbent materials used in disposable absorbent products for absorbing body fluid. For example, absorbent materials such as cellulose fibers, wood pulp, regenerated cellulose or cotton fibers. Such fibers may be chemically or physically modified. The absorbent 16 may include any of the above fibers in combination with other materials, both natural and synthetic, such as hydrophilic foams, hydrophilic polymers or the like. Wood pulp is frequently the material of choice primarily because it is inexpensive and readily available. The absorbent 16 may also include a thin absorbent layer of material such as tissue, fabric or the like made of cellulosic fibers.

The baffle 18 is usually designed to permit the passage of air and moisture vapor to the outer surface while blocking the passage of liquids. This prevents menstrual fluid, which may be expelled from the absorbent 16, from soiling the wearer or her clothing. The baffle 18 can be made from a polymeric film such as polyethylene, polypropylene, cellophane, or can be made from a bicomponent film. The baffle 18 can also be constructed from a liquid-permeable material that has been treated or coated to become liquid impervious. The first absorbent pad 12 includes an adhesive 28 for securing the first absorbent pad 12 to the crotch portion of a wearer's undergarment. The adhesive is positioned adjacent to the garment side of the baffle 18. The adhesive 28 is preferably a conventional pressure sensitive adhesive having a release paper 30 which may be removed to expose the adhesive 28 for attachment to the undergarment.

It is to be understood that the illustrated absorbent assembly is only one possible embodiment. Other possible embodiments include one in which an absorbent 16 is essentially completely wrapped with a cover 20 before it is placed on a baffle 18. The absorbent 16 can also include an absorbent core which possesses sufficient integrity to stand alone and which is fluid permeable on one surface while the other surface has been treated to render it liquid impervious.

Referring again to FIG. 1, the first absorbent pad 12 and second absorbent pad 14 are relatively superposed with the second absorbent pad 14 overlying the body-facing surface of the cover 20. The first absorbent pad 12 and the second absorbent pad 14 each have a centrally positioned longitudinal axis $LA_1$ and $LA_2$, respectively, which are illustrated as being coaxially aligned and collectively referred to in FIG. 1 as $LA_1$ and $LA_2$. The first absorbent pad 12 and the second absorbent pad 14 are physically separate from each other throughout their common interface. Surprisingly, the separation allows the absorbent pads to independently respond to the tortional forces exerted upon each pad. For example, the first absorbent pad 12 can respond to the dynamics of the undergarment without affecting the position and performance of the smaller, second absorbent pad 14 residing adjacent the wearer's body.

The first absorbent pad 12 is designed to be positioned in the crotch portion of a wearer's undergarment. Typically, the first absorbent pad 12 has a width, as measured at the pad's widest point, of between about 25 millimeters to about 150 millimeters, and preferably from about 50 millimeters to about 100 millimeters. The first absorbent pad 12 has a length $L_1$ as measured along a longitudinal edge of the pad 12 of between about 100 millimeters to about 400 millimeters and preferably from about 180 millimeters to about 400 millimeters and most preferably from about 200 millimeters to about 350 millimeters.

The second absorbent pad 14, which preferably is dimensionally smaller than the first absorbent pad 12, is designed to be worn next to the wearer's body and in direct contact with the vagina. The second absorbent pad 14 is preferably made narrower and shorter than the first absorbent pad 12. The second absorbent pad 14 need not have an absorbent capacity much greater than the total amount of menstrual fluid anticipated to be absorbed. This allows the second absorbent pad 14, in addition to being smaller, to be relatively thin. It should be noted that the second absorbent pad 14 is effective because the overall configuration and use of the sanitary napkin 10 results in the second absorbent pad 14 being maintained in close proximity to the wearer's vagina. Such proximity places it precisely where it should, very near the vaginal opening. Specifically, when the sanitary napkin assembly 10 is properly positioned by the user, the second absorbent pad 14 is self-positioning to a high degree next to the wearer's vulva. By virtue of the compositional nature of the article, occluding capabilities as regards to the prevention of fluid flow from the rearward area of the vestibule is highly efficient. While technically not a true seal, the normal motion of the user (e.g., walking, running, etc.) tends to reinforce the sealing or occluding affect of the second absorbent pad 14 within its zone of engagement with the rearward most aspect of the vestibule, thus "sealing" that area. Thus, as a general consequence a highly conformed anatomical fit is achieved, that fit relies in part upon the anatomy of the user and is generally self-adjusting. Thus, the second absorbent pad 14 can absorb a majority of the menstrual fluid. This will reduce the possibility of body fluid passing over the edges of the second absorbent pad 14. It also adapts better to the body, is more comfortable to the wearer and will be less noticeable through the clothes of the wearer. Accordingly, the second absorbent pad 14 has a width which ranges from between about 25 millimeters to about 120 millimeters, preferably from about 25 mm to about 100 mm and most preferably from about 40 mm to about 80 mm. The second absorbent pad 14 has a length which ranges from about 50 millimeters to about 200 millimeters, preferably from about 50 mm to about 170 mm and most preferably from about 50 mm to about 150 mm. Preferably, the length of the second absorbent pad 14 is chosen so that, when in use, the second absorbent pad 14 does not extend beyond either end of the first absorbent pad 12 without disengaging therefrom.

The first and second absorbent pads 12 and 14 shown in their most preferred embodiment have a generally ovate geometry. However, the absorbent pads can have an hourglass, racetrack or any other shape well known to those skilled in the sanitary napkin art.

Referring to FIGS. 2–3C, the securement device 28 has a first member 32 affixed to the first absorbent pad 12 and a second member 34 affixed to the second absorbent pad 14. The first and second members, 32 and 34 are adapted to moveably engage one another and preferably are designed so that the two members 32 and 34 are separate or readily separable from each other. Advantageously, this allows the first and second absorbent pads, 12 and 14 to be disengaged and used separately in cases where the amount of body fluid is small. This also gives the wearer an increased feeling of comfort during periods when smaller amounts of body fluids are secreted. The first member 32 has a flat, bottom surface 36 which is affixed to the body-facing surface of the cover 20 along the longitudinal axis $LA_1$ of the first absorbent pad 12. The first member 32 also includes a pair of vertical side walls 38 and 40 extending upward from the bottom surface 36. A pair of shoulders 42 and 44 depend from the side walls 38 and 40 which collectively form a horizontal slot.

The second member 34 is affixed to the garment-facing surface of the bottom layer and along the longitudinal axis $LA_2$ of the second absorbent pad 14. Typically, this bottom layer is the second baffle 26 of the second absorbent pad 14. The second member 34, shown in FIG. 3B, is generally circular in shape and contains a channel 46 for engaging the shoulders 42 and 44 of the first member 32. The channel 46 generally extends the circumference of the second member 34, thereby allowing the second absorbent pad 14 to independently be repositioned relative to the first absorbent pad 12. Although depicted in the preferred embodiment, the second member 34 can be any geometric shape, such as oval, rectangular, etc. that would allow the second member 34 to movably engage the first member 32.

Referring to FIGS. 2–6, the securement device 28 allows the first absorbent pad 12 and the second absorbent pad 14 to move independently relative to each other in at least one direction, i.e. longitudinally or transversely. As used herein the term "transversely" refers to a line, axis or direction which lies within the plane of the absorbent pad that is generally perpendicular to the longitudinal direction. Preferably, the securement device 28 allows the first and second absorbent pads, 12 and 14 respectively, to move independently in the longitudinal direction along at least one of the longitudinal axes $LA_1$ or $LA_2$, which can best be seen in FIG. 6. The first member 32 generally, has a sufficient length, $L_m$ so that when the second member 34 is engaged therewith, the second absorbent pad 14 can be slidably adjusted and positioned adjacent to the vulvar region of the wearer. In a preferred embodiment, the first and second members 32 and 34 are positioned on their respective absorbent pads 12 and 14 so that the second absorbent pad 14 will not project beyond one end of the first absorbent pad 12 without the second member 34 becoming disengaged from the first member 32. In a more preferred embodiment, the first and second members, 32 and 34 respectively, can be slidably adjusted along one of the longitudinal axes $LA_1$ or $LA_2$ up to a distance of about 25% of the total length $L_1$, (as best seen in FIG. 1), of the first absorbent pad 12.

In a preferred embodiment, the securement device 28 allows the absorbent pads 12 and 14 to rotate in both directions through an angle alpha ($\alpha$) of about 90°, as measured relative to their respective central longitudinal axis $LA_1$ and $LA_2$. Preferably, the securement device 28 allows the first and second absorbent pads 12 and 14 to rotate through an angle alpha (a) of about 45° and most preferably through an angle of about 25°. This is advantageous in that the securement device 28 allows the second absorbent pad 14 to be readily adjusted by the user when she positions the sanitary napkin 10 in her undergarment. This also permits the second absorbent pad 14 to respond to motions of the wearer and reposition itself relative to the first absorbent pad 12 without being adversely effected by the undergarment dynamics. However, it is expected that during use the second absorbent pad 14 will rotate less than about 20° relative to the longitudinal axis $LA_1$ of the first absorbent pad 12.

The first and second members 32 and 34 can be constructed of thermoplastic materials and desirably materials having a coefficient of friction ranging from about 0.02 to about 0.4. Suitable materials include polytetrafluouroethylene, polyethylene, nylon and the like. The low coefficient of friction of the construction materials permits the first absorbent pad 12 and the second absorbent pad 14, to which the first and second member, 32 and 34 respectively, are attached to easily move relative to each other. The first and second members 32 and 34 respectively, can be manufactured using methods well known in the thermoforming plastics art, such as injection molding and extrusion.

The first and second members, 32 and 34 can be affixed to their respective absorbent pads 12 and 14 by means well known in the art. For example, construction adhesive, ultrasonics, heat bonding and the like can be used.

Referring to FIGS. 4A–4C, another embodiment of the securement device 100 is shown. The securement device 100 includes a first member 110 and a second member 112. The first and second members, 110 and 112, are similar to the first and second members 32 and 34 shown in FIGS. 3A–3C, except for the following. The first member 110 includes a complimentary interlocking, longitudinally-extending female groove 114. The second member 112 includes a male rib 116 of a zipper type construction. Referring to FIG. 4C, the male rib 116 of the second member 112 operatively engages the female groove 114 of the first member 110 to secure the first and second absorbent pads 12 and 14, as seen in FIG. 1, together. The first and second members 110 and 112 move relative to each other longitudinally along the direction of the female groove. The groove/rib zipper construction utilized herein is further described in U.S. Pat. No. 5,192,135 issued to Woods et al. on Mar. 9, 1993; 5,138,750 issued to Gundlach et al. on Aug. 18, 1992; and 4,846,585 issued to Boeckmann et al. on Jul. 11, 1989, the entire disclosure of each being incorporated herein and made a part hereof. The zipper like members are available from Minigrip, Inc. located at Orangeburg, N.Y.

Figure 5:
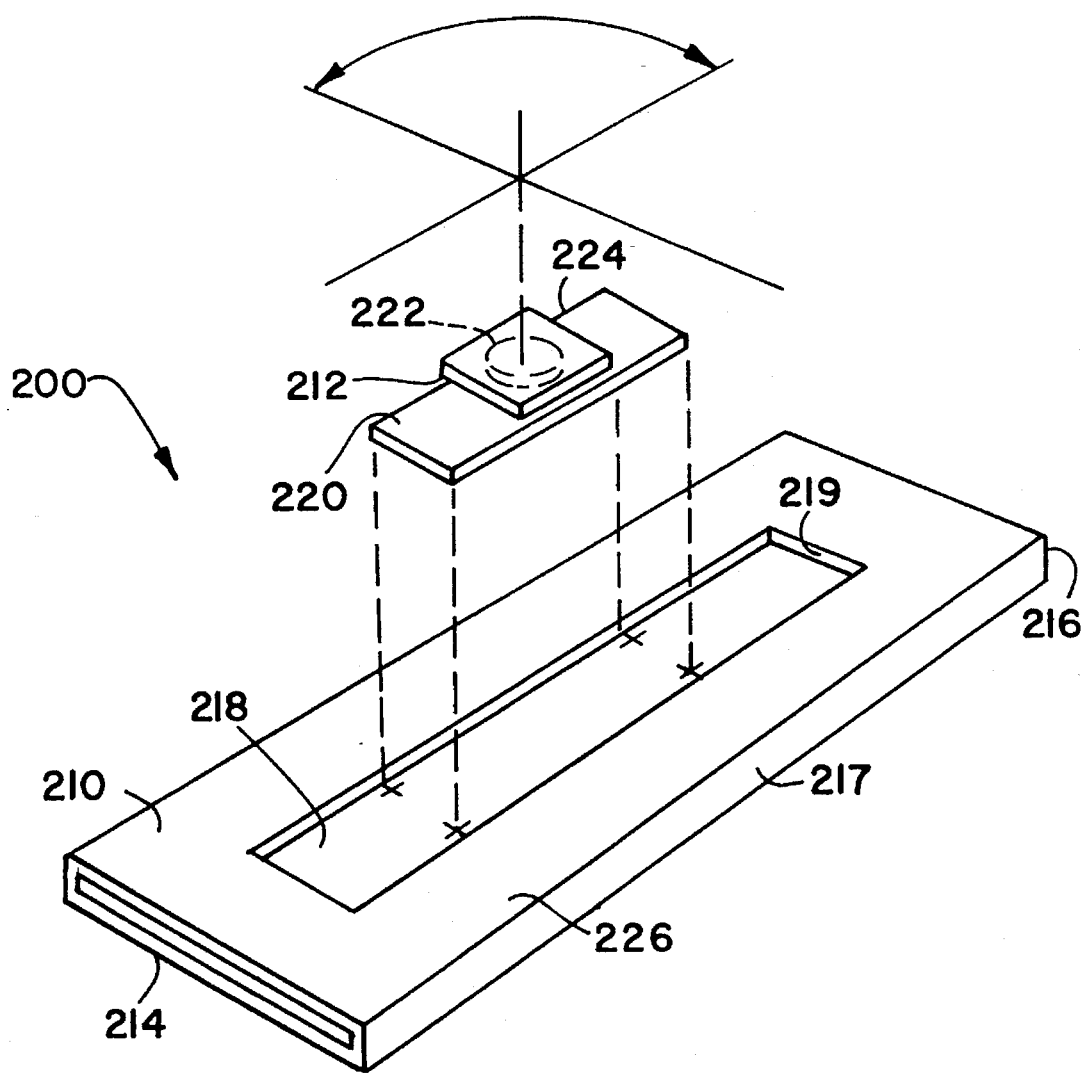
FIG. 5 is an exploded view of another embodiment of the securement device.
Figure 6:
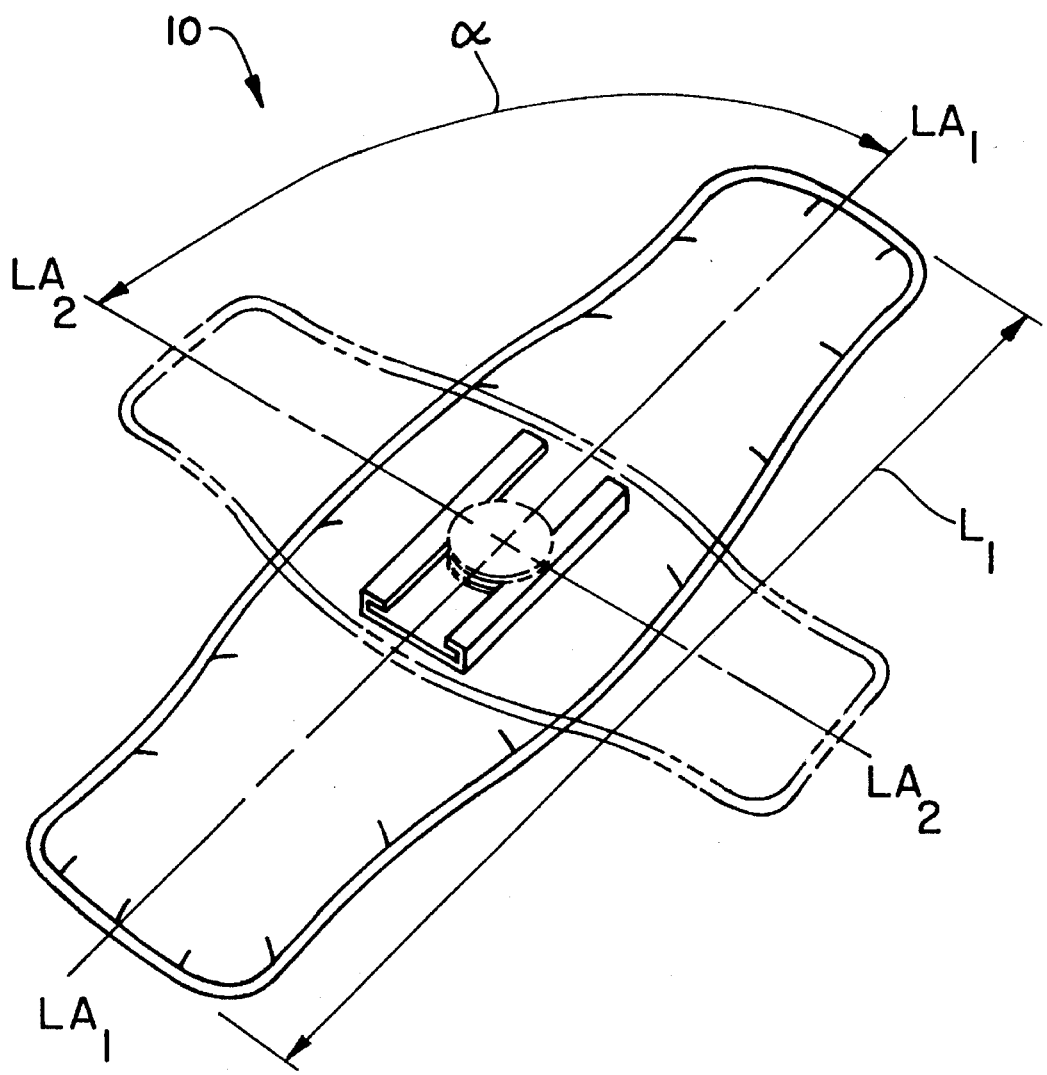
FIG. 6 is a top plan view showing the rotational movement of the securement device of FIG. 3C. The second pad, which normally obscures the attachment device, is shown in phantom.

Referring to FIG. 5, another embodiment of the securement device 200 is shown. The securement device 200 includes a first member 210 and a second member 212. The first member 210 includes a first end 214, a distal second end 216 and an outer periphery 217. Positioned centrally in the first member 210 is a slot 218 that is defined by the inner walls 219. The slot 218 lies between the first end 214 and the second end 216 and is designed so that the second member 212 can be disengagably connected to the first member 210. The length of the first member 210 is similar to that described above for the first member 32 of FIG. 3A.

The second member 212 includes a base 220, a neck 222 and a mounting platform 224. The base 220 has a width which is slightly less than the width of the slot 218 so that it may demountably engage the first member 210. The length of the neck 222 is slightly longer than the thickness of the first member 210 and the width of the base 220 is less than the width of the first member 210 so that the base 220 may be rotated 90° to secure the second member 212 to the first member 210. The platform 224 is sized so that when the base 220 is rotated 90°, allowing the second member 212 to engage with the first member 210, the platform 224 will reside above an upper surface 226 of the first member 210. This allows the second member 212 to be more accurately positioned into the slot 218 of the first member 210. Alternatively, the second member 212 can be constructed so that the base 220 of the second member 212 engages the first member 32 as seen in FIG. 3A. The base 220 would engage between the flat bottom surface 36 and the shoulders 42 and 44. This arrangement would limit the degree of rotation but would still allow the second member 212 to slidably adjust along the length of the flat bottom surface 36.

While the invention has been described in conjunction with several specific embodiments, it is to be understood that many alternatives, modifications, and variations will be apparent to those skilled in the art in light of the foregoing description. Accordingly, this invention is intended to embrace all such alternatives, modifications and variations which fall within the spirit and scope of the appended claims.

We claim:

1. An absorbent article assembly comprising:
   (a) a first absorbent pad having a predetermined length and a centrally positioned, first longitudinal axis;
   (b) a second absorbent pad superposed relative to said first absorbent pad, and said second absorbent pad having a centrally positioned, second longitudinal axis; and
   (c) securement means for movably securing said second absorbent pad to said first absorbent pad, said securing means including a first member and a second member, said first member being secured to said first absorbent pad along said first longitudinal axis and said second member being secured to said second absorbent pad along said second longitudinal axis, wherein said securement means allows said second absorbent pad to be slidably repositioned, independent of said first absorbent pad, along said first longitudinal axis.

2. The assembly of claim 1 wherein said second absorbent pad can be repositioned along said first longitudinal axis by a distance of up to about 25 percent of said length of said first absorbent pad.

3. The assembly of claim 1 wherein said first and second members are capable of rotating through an arc of about 45 degrees, as measured between said first and second longitudinal axes.

4. The assembly of claim 1 wherein said first and second members are capable of rotating through an arc of about 90 degrees, as measured between said first and second longitudinal axes.

5. A sanitary napkin assembly comprising:
   (a) a first absorbent pad having an absorbent with a body-facing surface and a garment-facing surface and a baffle positioned adjacent to said garment-facing side, said first pad having a centrally positioned, first longitudinal axis;
   (b) a second absorbent pad superposed relative to said first absorbent pad, said second absorbent pad having a second absorbent and a second baffle, said second baffle being positioned above said body-facing surface of said first absorbent, and said second absorbent pad having a centrally positioned, second longitudinal axis; and
   (c) securement means for movably securing said second absorbent pad to said first absorbent pad, said securing means being positioned intermediate said first and second absorbent pads and including a first member and a second member adapted to be slidably engaged with said first member, said first member being secured to said body-facing surface of said first absorbent pad and positioned along said first, longitudinal axis and said second member being secured to said second baffle and positioned along said second, longitudinal axis, wherein said securement means allows said second absorbent pad to move relative to said first absorbent pad.

6. The assembly of claim 5 wherein said second baffle of said second absorbent pad is apertured.

7. The assembly of claim 5 wherein said first absorbent pad has a predetermined length and said second absorbent pad can be repositioned along said first longitudinal axis by a distance of up to about 25 percent of said length of said first absorbent pad.

8. The assembly of claim 5 wherein said first and second members are demountably engaged.

9. The assembly of claim 8 wherein said second member has a channel and said first member has a pair of shoulders, wherein said channel at least partially resides intermediate said shoulders.

10. The assembly of claim 8 wherein said first member has a longitudinally-extending female groove and said second member has a male rib, said rib designed to interlock with said channel but allowing movement along said groove.

11. The assembly of claim 9 wherein said first and second members are capable of rotating through an arc of about 90 degrees, as measured between said first and second longitudinal axes.

* * * * *